United States Patent [19]

Aegerter, Jr. et al.

[11] Patent Number: 5,118,857
[45] Date of Patent: Jun. 2, 1992

[54] POLAR SOLVENT TREATMENT OF N-DODECYL MERCAPTOETHANOL

[75] Inventors: Paul A. Aegerter, Jr.; Jim D. Byers, both of Bartlesville, Okla.

[73] Assignee: Phillips Petroleum Company, Bartlesville, Okla.

[21] Appl. No.: 550,259

[22] Filed: Jul. 9, 1990

[51] Int. Cl.⁵ .......................... C07C 319/00
[52] U.S. Cl. ................................ 568/55
[58] Field of Search ........................ 568/55

[56] References Cited

U.S. PATENT DOCUMENTS 4,847,420  7/1989  Labat ........................ 568/55

OTHER PUBLICATIONS

Chemical Abstract, 83: 95961, 1975.
Chemical Abstract, 99: 157545, 1983.
Chemical Abstract, 107: 77079, 1987.

*Primary Examiner*—Patricia L. Morris
*Assistant Examiner*—Robert C. Whittenbaugh
*Attorney, Agent, or Firm*—Gary L. Haag

[57] ABSTRACT

The color and odor of n-dodecyl mercaptoethanol made using a triethylamine catalyst are improved by contacting crude n-dodecyl mercaptoethanol with a polar organic solvent having a boiling point of within about ±15° C. of the boiling point of triethylamine and heating said components under at least a partial vacuum.

12 Claims, No Drawings

POLAR SOLVENT TREATMENT OF N-DODECYL MERCAPTOETHANOL

BACKGROUND OF THE INVENTION

This invention relates to the polar solvent treatment of n-dodecyl mercaptoethanol (DMD-1) made with a triethylamine (TEA) catalyst.

The reaction between ethylene oxide and n-dodecyl mercaptan giving n-dodecyl mercaptoethanol using a basic catalyst is a well known. N-dodecyl mercaptoethanol is desirable because of its value as a specialty chemical and its use in the preparation of many products. Basic catalysts are generally preferred in the production of n-dodecyl mercaptoethanol because basic catalysts allow for the desired consumption of the mercaptan reactant before forming polyethylene glycols and dioxanes.

Purification of the n-dodecyl mercaptoethanol and the general removal of residual basic catalyst after completion of the reaction is one of the problems encountered in n-dodecyl mercaptoethanol production. Purification through distillation at high temperatures is typically not performed because n-dodecyl mercaptoethanol decomposes at high temperatures, and therefore would require a high vacuum system for distillation. Because such high vacuum systems are not generally available on a commercial, large-scale operation, an alternative purification scheme allowing the stripping of the residual catalyst is necessary.

Sodium hydroxide is commonly used as the basic catalyst in the reaction of ethylene oxide with n-dodecyl mercaptan to form the n-dodecyl mercaptoethanol. The sodium hydroxide has good catalytic activity, but the purification of the product away from the residual catalyst has been found to be difficult. Leaving the residual sodium hydroxide catalyst with the product is not practical because the sodium hydroxide forms a noticeable residue in the product. One method of stripping the residual catalyst from the product involves converting the sodium hydroxide into sodium bicarbonate which is in turn removed by filtration. This method, however, is time-consuming. Another method involves using water to wash the sodium hydroxide from the product, but this is unsatisfactory because undesirable water is left in the product. Thus, although production of n-dodecyl mercaptoethanol is possible with the sodium hydroxide catalyst, alternative catalytic methods are desirable.

Use of the basic catalyst system employing triethylamine as the catalyst represents one alternative to the sodium hydroxide system for production of n-dodecyl mercaptoethanol, as shown in the art in Chemical Abstracts 83: 95961; 99: 157545; and 107: 77079. The purification problem, however, is even more emphasized with the use of the triethylamine catalyst. The residual catalyst and other amine impurities formed during the reaction leave the n-dodecyl mercaptoethanol product with a very unpleasant and offensive odor in addition to leaving the n-dodecyl mercaptoethanol discolored. Pure n-dodecyl mercaptoethanol is found as a white, waxy solid with the low melting point of 33° C. The impurities found in the n-dodecyl mercaptoethanol produced using the triethylamine catalyst leave the compound with an undesirable yellow-brownish color. Thus, although TEA represents a very useful catalyst in terms of producing n-dodecyl mercaptoethanol, the n-dodecyl mercaptoethanol is left commercially undesirable because of residual amine impurities.

Various unsuccessful efforts have been made in the attempt to remov the offensive odor and undesired coloration left when TEA is used as a catalyst. For example, when the crude n-dodecyl mercaptoethanol is contacted with the polar solvent methanol (Boiling Point 69° C.), followed by heat under vacuum, neither the color nor odor improved. Similarly, the non-polar solvent heptane (Boiling Point 98.4° C.) also failed to correct the odor and color problems of the crude n-dodecyl mercaptoethanol. Further, the use of nitrogen as a gaseous stripping agent is also ineffective against the odor and coloration problems.

SUMMARY OF THE INVENTION

It is an object of this invention to allow the use of triethylamine as a catalyst for the production of n-dodecyl mercaptoethanol.

It is a further object of this invention to remove the offensive odor and undesirable discoloration associated with the use of triethylamine as a catalyst for the production of n-dodecyl mercaptoethanol.

It is still a further object of this invention to provide a superior n-dodecyl mercaptoethanol product.

In accordance with this invention, a n-dodecyl mercaptoethanol prepared with a triethylamine catalyst is contacted with a polar organic solvent having a boiling point within about ±15° C. of the boiling point of the triethylamine and said components are exposed to heat under at least a partial vacuum thereby at least partially driving off said solvent and impurities.

DETAILED DESCRIPTION OF THE INVENTION

It has been discovered that the undesired offensive odor and undesired coloration of n-dodecyl mercaptoethanol formed by a triethylamine catalyzed reaction can be stripped from the product if the n-dodecyl mercaptoethanol is contacted with a polar organic solvent having a boiling point within about ±15° C. of the boiling of triethylamine (89° C.). The solvent and undesirable impurities are removed by heat under at least a partial vacuum upon contact.

In forming the crude n-dodecyl mercaptoethanol product, n-dodecyl mercaptan is reacted with ethylene oxide utilizing the triethylamine catalyst as follows:

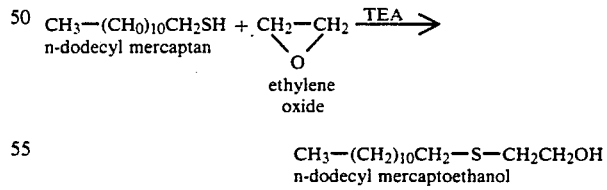

$$CH_3-(CH_2)_{10}CH_2-S-CH_2CH_2OH$$
n-dodecyl mercaptoethanol

This triethylamine catalyzed reaction is known in the art. The reaction temperature is generally approximately 140° C. The induction time of of the reaction is generally about 30 minutes. Upon the onset, the reaction proceeds essentially quantitatively consuming all of the n-dodecyl mercaptan present, assuming that at least a stoichiometric amount of ethylene oxide is present. The reaction should be stopped as soon as possible after the reaction is complete if excess ethylene oxide is used because polyethylene glycols and dioxanes may be formed otherwise. If excess ethylene oxide is used, it should not be used in amounts of greater than 10% excess.

The starting materials of n-dodecyl mercaptan, ethylene oxide, and triethylamine are each commercially available.

The crude n-dodecyl mercaptoethanol is defined as the reaction product and accompanying residue present after the n-dodecyl mercaptan, ethylene oxide, and triethylamine have been allowed to react together.

The polar organic solvent is selected from those polar compounds having a boiling point within about ±15° C. of the boiling point of the triethylamine boiling point of 89° C. In other words, those solvents having a boiling point between about 74° C. and 104° C. are preferred. More preferred solvents are the alcohols selected from the group consisting of 1-propanol, 2-propanol, and t-butanol. The most preferred solvent is 2-propanol.

The polar organic solvent should be present in a molar ratio of at least 1 mole of polar organic solvent per 20 moles of n-dodecyl mercaptoethanol, preferably 1 mole of polar organic solvent per 10 moles of n-dodecyl mercaptoethanol, and most preferably 1 mole of polar organic solvent per 1.5 moles of n-dodecyl mercaptoethanol. The solvent can actually be present in excess of 1 mole of solvent per 1.5 moles of n-dodecyl mercaptoethanol, but for economic reasons the most preferred ratio is set at 1:1.5.

The polar organic solvent can be contacted with the crude n-dodecyl mercaptoethanol in a batch or continuous process. If the solvent is contacted with crude n-dodecyl mercaptoethanol made in a batch reaction zone, the contacting can be made immediately after the n-dodecyl mercaptoethanol has been formed in the same reaction vessel or after the n-dodecyl mercaptoethanol has been recovered from the reaction vessel and stored. Preferably the solvent is introduced into the reaction vessel shortly after the product has been formed. To insure contact between the polar organic solvent and the n-dodecyl mercaptoethanol, the reaction vessel is preferably stirred. The vessel is generally heated gradually from approximately 25° C. to about 110° C. with the pressure being lowered, with at least a partial vacuum resulting. Preferably the pressure is taken from 100 mm Hg to maximum vacuum during the course of the polar organic solvent treatment. The upper limit of the heat application is 120° C. due to the risk of decomposing the n-dodecyl mercaptoethanol.

The polar organic solvent treatment includes both the contacting of the solvent with the n-dodecyl mercaptoethanol and the distillation solvent upon heat under at least a partial vacuum. This treatment may last from 0.1 minutes to 24 hours, preferably 1 to 5 hours, and most preferably about 2 hours. During this time period the heat under vacuum causes the solvent and the triethylamine catalyst residue and other undesirable amine impurities to be driven off in the distillate. The undesirable amine odor is noticeably absent upon completion of the treatment. The disappearance of the amine impurities can be monitored by gas chromatography.

The following examples provide further illustration of the invention and are, in no way, intended to limit the scope thereof.

EXAMPLE 1

Preparation of Crude N-Dodecyl Mercaptoethanol

The following shows the preparation of n-dodecyl mercaptan using a stoichiometric amount of ethylene oxide.

To a 1 gallon stainless steel reactor was added:
n-dodecyl mercaptan: 1,616 g (8.0 moles)
triethylamine: 50 g (0.5 moles).

To a liter stainless steel bomb was added:
ethylene oxide: 353 g (8.0 moles).

The contents of the reactor containing the n-dodecyl mercaptan and triethylamine were stirred and heated to 120° C. A small amount of ethylene oxide was added to the reactor, and the reactor was then stirred for 45 minutes. When no reaction occurred, the heat was increased to 140° C. Within 20 minutes an exotherm was noted, accompanied by a pressure drop in the reactor. At this point, the remaining ethylene oxide was added in increments sufficient to hold the temperature of the reactor at below 150° C., with cooling. A sample of the crude n-dodecyl mercaptoethanol was taken from the reactor. The reaction product had a light brownish-yellow color and an easily perceptible offensive amine odor.

GLC analysis indicated that the n-dodecyl mercaptan was completely reacted, with no dioxanes or polyethylene glycols in evidence. The product GLC analysis was done using a Hewlett-Packard 5880 gas chromatograph equipped with a thermal conductivity detector. The product was analyzed using a 20"×⅛" stainless steel column containing 2% OV-101 on a 100–200 mesh WHP support from Supelco Inc., Bellefonte, Pa. The injection port was maintained at 300° C. and the detector was maintained at 325° C. The chromatograph was temperature programmed from 100° to 300° C. at 15° C./minute. The final temperature was held for 10 minutes.

2-Propanol Treatment

The crude n-dodecyl mercaptoethanol was treated by the inventive purification process using 2-propanol in the following manner:

To two parts of crude n-dodecyl mercaptoethanol (200 ml) was added one part by volume of 2-propanol (100 ml). The reactor had a temperature of 55° C. and pressure of 100 mm Hg upon contacting the n-dodecyl nercaptoethanol with the 2-propanol. After approximately 105 minutes of gradual heating and application of a vacuum, the temperature of the reactor measured 62° C. The vacuum was then taken to a maximum for another 15 minutes, with distillation of the solvent and impurities occurring throughout the heating. Upon completion of the treatment, 178 ml of the n-dodecyl mercaptoethanol were recovered. The offensive amine odor previously associated with the n-dodecyl mercaptoethanol was removed. Further, upon cooling the n-dodecyl mercaptoethanol was a waxy, whitish solid rather than original brownish-yellow.

An analysis of the treated product gave the following results:

| | | |
|---|---|---|
| Flash Point (COP) | ASTM D-93 | 176° C. (349° F.) |
| Density | ASTM D-4052 | 0.8811 g/ml @ 100° C. |
| Viscosity | ASTM D-445 | 2.86 cst @ 100° C. |
| Hydroxy Number | | 224.4 mg KOH/g |
| Mercaptan Sulfur | | 50 ppm |

| | |
|---|---|
| Sulfur (Total) | 12.47 wt. % |
| Melting Point | 33° C. |
| Color | white |
| n-dodecyl sulfide (contained) | 90.5% |

EXAMPLE 2

2-Propanol Treatment

Again, 2-propanol was used as a solvent using the same procedure as in Example I, the only difference being the ratio of solvent to crude n-dodecyl mercaptoethanol. Here, 200 ml of 2-propanol was added to 300 ml of crude n-dodecyl mercaptoethanol. These amounts also removed the offensive odor as well as bringing the color to a whitish waxy solid upon cooling.

CONTROLS

The following controls demonstrate the unexpected results reached when the amine odor and discoloration were removed from crude n-dodecyl mercaptoethanol using the inventive solvent 2-propanol as opposed to other solvents. As shown below, neither methanol not heptane were effective treatment agents.

Methanol (Boiling Point 69° C.)

In a similar procedure as recited for 2-propanol in Example I, the crude n-dodecyl mercaptoethanol was treated with the solvent methanol rather than the inventive 2-propanol. Following similar steps, as shown in Example I, 100 ml of methanol were contacted with 200 ml of crude n-dodecyl mercaptoethanol and heated under vacuum thereafter. After completion of the treatment, 172 ml of n-dodecyl mercaptoethanol were recovered. The treated n-dodecyl mercaptoethanol still contained the offensive amine odor and discoloration. The low boiling point solvent methanol was not effective as a treatment agent.

Heptane (Non-Polar Solvent)

Approximately 1748 g of crude n-dodecyl mercaptoethanol was melted and added to a distillation flask along with 750 ml of the non-polar solvent heptane. The mixture was then vacuum stripped on a large vigreaux column for approximately 1 hour at 100° C. After the completion of the treatment, 700 g of heptane was recovered along with 1734 g of crude n-dodecyl mercaptoethanol. The treated n-dodecyl mercaptoethanol still contained the offensive amine odor and discoloration. The non-polar solvent heptane was not effective as a treatment agent.

That which is claimed is:

1. A method for treating crude n-dodecyl mercaptoethanol prepared by contacting n-dodecyl mercaptan with ethylene oxide in the presence of triethylamine comprising the steps:
    (a) contacting said crude n-dodecyl mercaptoethanol with a polar organic solvent or mixture of polar organic solvents having a boiling point within about ±15° C. of the triethylamine boiling point; and
    (b) exposing resulting mixture from step (a) to heat under at least a partial vacuum thereby at least partially driving off said polar organic solvent or solvents and impurities and obtaining a treated n-dodecyl mercaptoethanol product.

2. A method according to claim 1 wherein said polar organic solvent is present in a molar ratio of at least 1 mole of polar organic solvent per 20 moles of n-dodecyl mercaptoethanol; and said heat does not exceed 120° C.

3. A method according to claim 2 wherein said polar organic solvent is an alcohol selected from the group consisting of 1-propanol, 2-propanol, and t-butanol, and said molar ratio is at least 1 mole of polar organic solvent per 10 moles of n-dodecyl mercaptoethanol.

4. A method according to claim 3 wherein said alcohol is 2-propanol and said molar ratio is at least 1 mole of polar organic solvent per 1.5 moles of n-dodecyl mercaptoethanol.

5. A method according to claim 1 wherein said n-dodecyl mercaptoethanol is produced by contacting n-dodecyl mercaptan and ethylene oxide in the presence of said triethylamine in a batch reaction zone and thereafter said polar oganic solvent is added.

6. A method according to claim 5 wherein said n-dodecyl mercaptoethanol is contacted with said polar organic solvent immediately after being formed.

7. A method according to claim 5 wherein said n-dodecyl mercaptoethanol is stored prior to said contacting with said organic solvent.

8. A method according to claim 1 wherein said polar organic solvent is an alcohol selected from the group consisting of 1-propanol, 2-propanol, and t-butanol; and said molar ratio is at least one mole of polar organic solvent per 10 moles of n-dodecyl mercaptoethanol.

9. A method according to claim 8 wherein said alcohol is 2-propanol and said molar ratio is at least one mole of polar organic solvent per 1.5 moles of n-dodecyl mercaptoethanol.

10. A method according to claim 1 wherein said n-dodecyl mercaptoethanol is produced by contacting n-dodecyl mercaptan and ethylene oxide in the presence of triethylamine in a batch reaction zone and thereafter said polar organic solvent is added.

11. A method according to claim 10 wherein said n-dodecyl mercaptoethanol is contacted with said polar organic solvent immediately after being formed.

12. A method according to claim 10 wherein said n-dodecyl mercaptoethanol is stored prior to said contacting with said organic solvent.

* * * * *